(12) United States Patent
Gaytan

(10) Patent No.: US 7,157,094 B2
(45) Date of Patent: Jan. 2, 2007

(54) GRANULATED ACTIVE INGREDIENTS

(75) Inventor: Jesse Gaytan, Valdosta, GA (US)

(73) Assignee: Arysta LifeScience North America Group, Salt Lake City, UT (US)

( * ) Notice: Subject to any disclaimer, the term of this patent is extended or adjusted under 35 U.S.C. 154(b) by 660 days.

(21) Appl. No.: 09/801,871

(22) Filed: Mar. 9, 2001

(65) Prior Publication Data

US 2006/0255490 A1    Nov. 16, 2006

(51) Int. Cl.
*A01N 25/12*    (2006.01)

(52) U.S. Cl. ............... 424/408; 424/405; 424/406; 424/409; 424/417; 514/120

(58) Field of Classification Search ............... 514/120; 424/405, 408, 409, 417
See application file for complete search history.

(56) References Cited

U.S. PATENT DOCUMENTS

| | | |
|---|---|---|
| 3,716,600 A | 2/1973 | Magee |
| 3,845,172 A | 10/1974 | Magee |
| 3,914,417 A | 10/1975 | Magee |
| 4,049,679 A | 9/1977 | Magee |
| 4,110,443 A | 8/1978 | Magee |
| 4,150,155 A | 4/1979 | Kishino et al. |
| 4,218,444 A | 8/1980 | Koundakjian |
| 4,450,158 A | 5/1984 | Fahmy |
| 4,544,553 A | 10/1985 | Smolanoff et al. |
| 4,554,155 A | 11/1985 | Allan et al. |
| 4,614,734 A | 9/1986 | Smolanoff et al. |
| 4,940,556 A | 7/1990 | MacFarlane et al. |
| 5,075,058 A | 12/1991 | Chan et al. |
| 5,100,667 A | 3/1992 | Chan et al. |
| 5,140,019 A | 8/1992 | Wada et al. |
| 5,165,934 A | 11/1992 | Wada et al. |
| 5,190,764 A | 3/1993 | Chiba et al. |
| 5,260,312 A | 11/1993 | Wada et al. |
| 5,298,501 A | 3/1994 | Cummings |
| 5,352,674 A | 10/1994 | Cummings |
| 5,369,100 A | 11/1994 | Cummings |
| 5,443,674 A | 8/1995 | Fresonke |
| 5,443,764 A | 8/1995 | Lloyd et al. |
| 5,464,623 A | 11/1995 | Chan et al. |
| 5,521,176 A | 5/1996 | Wada et al. |
| 5,622,658 A | 4/1997 | Lloyd et al. |
| 5,650,163 A | 7/1997 | Cannelongo |
| 6,013,272 A | 1/2000 | Cummings et al. |
| 6,177,412 B1 | 1/2001 | Kincade et al. |
| 6,200,961 B1 | 3/2001 | Kostka et al. |
| 6,335,026 B1 | 1/2002 | Katayama |
| 6,337,323 B1 | 1/2002 | Cummings |
| 6,337,332 B1 | 1/2002 | Carpino |

FOREIGN PATENT DOCUMENTS

| | | |
|---|---|---|
| JP | 03-023521 (B2) | 3/1991 |
| JP | 06-092803 (A1) | 4/1994 |
| JP | 07-002610 (A1) | 1/1995 |
| JP | 07-002611 (A1) | 1/1995 |
| JP | 07-291804 (A1) | 7/1995 |
| JP | 09-124406 (A1) | 5/1997 |
| WO | WO9716968 | 5/1997 |

OTHER PUBLICATIONS

ICI Dictionary ,6th edition, pp. 774, 775 1995.*
"POLYOX Water Soluble Resins", Dow Chemical Company (Mar. 2002).
"Water Granulation with Polyox WSR", Dow Chemical Company (Feb. 2003).
"Process For Granulating Polyethylene Oxide", http://www.priorartdatabase.com/ipcom/0000189400, (Aug. 21, 2003).
"Polyox Water Soluble Resins Resources", http://www.pow.com/polyox/resource/rsc_lit.htm, (2004).
"Polyox USR Solid Dosage Formulation Via Melt Extrusion", Dow Chemical Company (Feb. 2003).
"Solubility Characteristics of Polyox Water—Soluble Resins in Selected Solvents", Dow Chemical Company (Apr. 2002).
"Standard Grade Polyox Resins", Dow Chemical Company, copyright 1995-2004.

* cited by examiner

*Primary Examiner*—Neil S. Levy
(74) *Attorney, Agent, or Firm*—Roylance, Abrams, Berdo & Goodman, L.L.P.

(57) ABSTRACT

Granulated forms of various active ingredients can be prepared with a small amount of a dissolvable polymer and a solvent for that polymer. The solvent dissolves at least a portion of the polymer. This dissolved polymer acts as a particle lubricant for the extrusion process and, when the solvent is removed, as a binder for the final extrudate. A poly(alkylene oxide) is preferred and, in the presence of a small amount of solvent, dissolves sufficiently to provide lubricity to the extrusion mixture that the solids can be extruded with little friction and associated local temperature rise thru the extrusion die.

26 Claims, No Drawings

GRANULATED ACTIVE INGREDIENTS

FIELD OF THE INVENTION

The present invention relates to a method for extruding heat sensitive active ingredients in the form of finely divided solids, powders or crystals into larger granules bound together by a polymeric binder that also acts as a lubricant.

BACKGROUND TECHNOLOGY

Powdered materials can be compacted and formed into shapes of extended length by extrusion. Generally speaking, a progressively threaded extrusion screw is rotated at a preselected rate to convey a feed material into an enclosed section to an extrusion die opening. Frictional forces through the die opening resist the forward conveying action of the progressive screw and compact the feed material as it passes thru the die opening.

Inorganic materials, such as ceramics, can benefit from the heat and friction of the passage thru the die opening. Such ceramic extrudates are effectively dewatered and compacted sufficiently to form a wet "green" extrudate of sufficient integrity to withstand handling and more complete drying. Organic materials, however, can be severely degraded by the high temperatures encountered when passing thru an extrusion die. Such materials are either not extruded or require such slow extrusion screw speeds that the manufacturing process is limited in its production rate.

Many active ingredients are in the form of powders, free flowing crystals, or other types of finely divided solids. Such active ingredients are, for many applications, most useful in the form of larger aggregates or granules. A variety of granulation methods can be used to process such materials.

Granulation of heat sensitive active ingredients has traditionally excluded the use of extrusion and other high shear types of granulation methods due to high temperature rises at the die. It is not uncommon for some extruders operating at normal, commercial extrusion rates to expose the extruded material to temperature increases of 25° to 100° C. This is acceptable for extruded ingredients that are not degraded or otherwise harmed by such temperatures but can be disastrous for organic or biologic active ingredients that cannot withstand such temperatures. Thus, the controls and manufacturing efficiencies that attend extrusion techniques. It would be desirable to have an extrusion process for heat sensitive active ingredients that did not expose the extruded active ingredient to deleterious temperature increases at the extrusion die but which would form adequately dense extrudates at a commercially acceptable rate.

High temperatures have also prevented many useful pest control agents, herbicides, and plant growth regulating agents from being offered as a granule. Such materials are often chemical compounds that contain heat sensitive linkages that would be harmed by exposure to elevated temperatures.

N-hydrocarboyl phosphoroamidothioates and phosphoroamidodithioates (referred to herein as "phosphoroamido(di)thioates") are classes of particularly heat sensitive compounds that are used as systemic insecticides in a variety of environments. One of the most commercially important compounds within this class is acephate. Acephate and related compounds are described in U.S. Pat. Nos. 3,716,600, 3,845,172 and 3,914,417.

Orthene® is a commercial form of acephate that is produced as a technical grade chemical of about 97 to 99.5% purity. It is available as a liquid and fine powder. The formation of a pellet or granular form with commercially acceptable properties has, thus far, eluded the art despite significant efforts.

Chevron and Valent have received a number of patents for processes to manufacture pelleted or granular acephate. Chan et al. U.S. Pat. No. 5,075,058 describes phosphoroamido(di)thioate pellets with a second active ingredient (insecticide, fungicide, herbicide, or fertilizer), a surfactant that is used to encapsulate the phosphoroamido(di)thioate active, an anhydrous magnesium sulfate as a dehydrating agent to absorb moisture and prevent hydrolysis of the phosphoroamido(di)thioate, a deodorant, and an anti-foaming agent. The mix is extruded thru a die at 91–100° F. and dried.

Chan et al. U.S. Pat. No. 5,100,667 describes a solvent-free method for making phosphoroamido(di)thioate pellets that relies on a dry mix with a solid surfactant to provide structural integrity. The example shows the use of ammonium sulfate in addition to the phosphoroamido(di)thioate and surfactant.

Chan et al. U.S. Pat. No. 5,464,623 teaches two processes to pelletize phosphoroamido(di)thioates. One uses a solvent for the technical to make a pourable or extrudable mixture. The list of preferred solvents include hexane, carbon tetrachloride, toluene, isopropanol, ethanol, chloroform, methanol, and methylene chloride. The other process avoids use of a solvent and melts the technical at about 90° C. for subsequent molding or spraying into droplets.

Cummings U.S. Pat. No. 5,298,501 describes the use of 83–98 wt % ammonium sulfate for providing integrity to granules containing 2–17 wt % of a phosphoroamido(di)thioate.

Cummings U.S. Pat. No. 5,352,674 discloses a formulation containing a phosphoroamido(di)thioate, an optional second active ingredient (e.g., a fungicide), at least 75 wt % of ammonium sulfate, 0.2–5 wt % of a surfactant, 0.05–2 wt % of a deodorant, and 1–5 wt % of granular processing aids that are selected from a lubricant (Mg stearate, Ca stearate, Zn stearate, and silicon emulsions) in an amount within the range of 0.5–5 wt %, a binder (corn starch, polymers, and natural gums), and 0.5–5 wt % of a flowability aid (colloidal silica, and micronized clay). All examples use significant quantities of ammonium sulfate to form a structural granule. Indeed, example 3 of the '674 patent illustrate the adverse storage effects of formulations that do not contain ammonium sulfate.

Cummings U.S. Pat. No. 5,369,100 is directed to a formulation that does not use a binder. Instead, the formulation relies on compaction of a mix containing the technical form of the active an ammonium sulfate. Lubricants (Mg stearate) and flow aids (silica particles) are also added to the formulation as shown in the examples.

Cummings et al. U.S. Pat. No. 6,013,272 teaches the manufacture of water-free phosphoroamido(di)thioate granules without added solvent by heating the extrusion die to a temperature that is sufficient to soften the active solids while controlling the rate at which water is added. Final products are disclosed as having a moisture level of less than 0.5 wt %. It is disclosed in column 5 that small amounts of a vinylpyrrolidone-vinyl acetate copolymer does not adversely affect the process and that the process does not require the use of surfactants or binding agents.

Unfortunately, the phosphoroamido(di)thioates can begin the degradation process under the effects of moisture (hydrolysis) or heat (oxidation). Either degradation mechanism can change the nature and amount of the insecticidally active compound into by-products that are not insecticidally effective. Thus, the moisture content of the final granule should be as low as possible and exposure to heat in processing or storage should be avoided, if possible. It would be beneficial to have an extrusion process for making granules from phosphoroamido(di)thioate solids and other solids adversely affected by heat or moisture without exposing these solids to high temperatures or high levels of residual moisture.

SUMMARY OF THE INVENTION

It is an objective of the invention to provide an extrusion process that does not subject the extruded material to high temperature rises at the die even when operated at normal, commercially economic speeds.

It is another objective of the invention to provide an extrusion process using a highly effective material that acts as both a lubricant in the extruder and a binder in the final product. Such a process can be run at ambient temperatures without cooling of the extrusion die or a controlled introduction of coolants or other liquids into the extruded formulation.

In accordance with these and other objectives of the invention that will become apparent from the description herein, the invention relates to a composition and its manufacturing process that includes the step of extruding at ambient temperatures a mixture comprising an active ingredient, a dissolvable polymeric lubricant/binder, an optional anticaking agent, and an amount of a solvent for said polymer that is sufficient to dissolve said polymeric lubricant/binder and form an extrudable composition of high lubricity.

The dissolved polymeric component acts as a lubricant during the extrusion process to reduce the frictional heat of the extrusion process. When extruded and processed to remove residual solvent, the polymeric component acts as a binder for the extruded components to enhance the structural integrity of the extrudate. For those active ingredients that are sensitive to heat, the granular solids can be dried to an acceptable solvent level by one or more methods that do not subject the active ingredient to unacceptably high temperatures or a solvent can be used with a sufficiently high vapor pressure to be removed at temperatures that are not harmful to the active ingredient within the granule. The preferred combination of polymer and solvent is a poly(alkylene oxide) and a small amount of water, e.g., less than 5 wt % or nonaqueous solvent for the poly(alkylene oxide).

The process of the invention provides extrudates of good density but without the history of exposure to heat or high water concentrations that are characteristic of prior art processes. The result is an extruded product and process with acceptable density, integrity, and durability but without heat exposure history.

DETAILED DESCRIPTION

The process of the invention allows active ingredients (solid or liquid on solid carrier) to be formed into extrudates with a small quantity of a dissolvable, polymeric lubricant/binder, an amount of solvent that is sufficient to dissolve at least some of the polymeric lubricant/binder, and an optional anti-caking agent. The high lubricity of the dissolved polymeric component reduces frictional forces (interparticle friction and friction at the edge of the die orifice) that would conventionally produce heat and expose the active ingredient to detrimentally high temperatures. The high lubricity of the dissolved polymeric component of the present invention allows the solids in the extruder mixture to slide past one another more easily and thereby reduce frictional heating without reducing the desirable compaction effects of an extruder. Frequently, the lubricity of the dissolved polymeric component is sufficient to allow extrusion without the need for temperature control or coolant introduction systems at the extrusion die. If desired, the extruded form can be cut to length and used without further processing or shaped into granules.

Unless otherwise noted, all percentages are by weight and are based on total weight.

The active ingredients that can be granulated in accordance with the invention can be selected from a wide variety of materials. Preferably, the active ingredients are solid particulates or liquids that are carried by inert or additionally active solid particulates. Those active ingredients that are sensitive to heat are well suited for extrusion according to the present invention.

Exemplary active ingredients are useful as pharmaceutical drugs, biologic agents (beneficial bacteria, inert viruses, and the like), and agrochemicals (agriculturally effective active ingredients with activity as herbicides, plant growth regulators, insecticides, fungicides, and essential plant minerals), detergents, and similar chemical compounds or formulations. Agrochemicals are particularly well suited for granulation according to the present invention.

Herbicides that can be extruded according to the invention include the triazines (e.g., atrazine), the ureas, glyphosate, sulfosate, glyfosinate, and sethoxydim.

Plant growth regulators that can be extruded include plant growth hormones such as at least one of the 84 identified gibberillins with $CA_3$, $GA_4$, $GA_5$, $CA_7$ and $GA_9$ being preferred; cytokinins (e.g., zeatin, kinetin, benzyladenine, dihydrozeatin, and isopentenyl adenine); auxins (e.g., indolacetic acid (IAA), indolebutyric acid (IBA), and naphthalenacetic acid (NAA)); sodium ortho-nitrophenolate; sodium para-nitrophenolate; sodium 5-nitro-guaicolate; and polyhydroxycarboxylic acids of 2, 4, 5, and 6 carbon structures; ethephon; chlormequat chloride; mepiquat chloride; and fertilizers. Such plant growth regulators affect and alter plant metabolic processes to enhance or retard plant growth.

Insecticides that can be extruded according to the present invention include materials and biological agents that control a target insect population through lethal ingestion, sterilization, or other interference with the insect life cycle. Exemplary insecticides include solid and liquid forms of the carbamates (e.g., carbaryl, aldicarb, methomyl, carbofuran, bendiocarb, oxamyl, thiodicarb, trimethylcarb); organophosphates (e.g., phorate, terbufos, fonophos, isofenphos, ethoprop, fenamiphos, disulfoton, malathion, parathion, demeton, dimethoate, chlorpyrifos, diazinon, and phosmet); compounds which break down the insect's digestive tract tissue including fluorine compounds (cryolite), zinc, and mercury; nicotine; rotenone; neem oil or azadiractin; natural or synthetic pyrethrins; petroleum oils; the halogenated hydrocarbons (e.g., endrin, aldrin and its epoxide, dieldrin, heptachlor, DDT, BHC, lindane, chlordane, methoxychlor, DDD, TDE, and the polychlorinated biphenyls); and microbials (e.g., *Bacillus thuringiensis* and entomopathic viruses such as insecticidal viruses such as the bacculo viruses).

Fungicides that will benefit from the mixtures of the invention 1 include tridemorph, metalaxyl, iprodione, fosetyl-aluminum, thiophanate, benomyl, triadimefon, carboxin, oxycarboxin, carbendazim, thiabendazole, thiophanate, ethirimol, bupirimate, dimethirimol, captan, any of the EBDCs (e.g., mancozeb, maneb, niram, metiram, zineb, and ferbam), chlorothalonil, iprodione, ziram, copper salts (e.g., copper sulfate and copper oxychloride), and sulfur. The invention is particularly well suited for encapsulating captan in particles having 55–80 wt % captan therein.

Other systemic agents for plants that benefit from the present invention include, inter alia, aldicarb, carbofuran, dimethoate, phorate, and terbufos, and the phosphoroamido(di)thioates.

The phosphoroamido(di)thioates that can be used in the invention include insecticidally active compounds having the general formula:

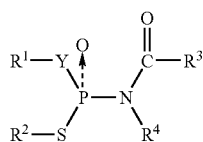

wherein:
R$^1$ and R$^2$ individually are an alkyl, alkenyl or alkynyl group containing up to 6 carbon atoms,
R$^3$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms,
R$^4$ is hydrogen or an alkyl group containing 1 to 6 carbon atoms, and
Y is oxygen or sulfur.

Acephate is a particularly preferred insecticide for use in the present invention. It is commercially available in a technical grade solid of at least 97 wt % purity and is used in granules of the present invention in an amount of at least 92 wt %, preferably at least 94 wt %, and most preferably in an amount of at least 95 wt % based on total weight of the dried granule.

The acephate is preferably milled before granulation. Details of the milling process are described in my copending application Ser. No. 60/279,433.

Essential plant minerals that can be encapsulated according to the invention include any of the minerals known to the art to effect plant growth in conventional amounts. Some examples include elemental and soluble salt forms of boron, nitrates, calcium, potassium, phosphates, iron, magnesium, sulfur, manganese, molybdenum, zinc, and copper.

The dissolvable polymers for use with the present invention are soluble in a solvent (e.g., water, dimethylsulfoxide, emulsions, alcohol-water azeotropes, or mixtures of these), solid at ambient temperatures, inert toward the active ingredient, and provide lubricity to the extrusion mixture upon at least partial dissolution in the inert solvent. Suitable dissolvable polymers for use in the present invention include one or more of the poly(alkylene oxides) (e.g., poly(ethylene oxide), poly(propylene oxide), and poly(butylene oxide)) with poly(ethylene oxide) being particularly preferred.

A particularly preferred lubricant/binder component for the present invention is poly (ethylene oxide) having an average molecular weight of less than about 50,000. A preferred average molecular weight is within the range from about 15,000 to about 35,000. Such materials are dry, free-flowing powders, completely soluble in water and certain organic solvents, and have crystalline melting points within the range of 63° to 67° C.

Useful amounts of the polymeric lubricant/binder is generally within the range from about 0.1–5 wt %, preferably 0.2–3 wt %, and more preferably 0.25–2 wt % based on total weight of the composition. When used in an amount within the range of 0.2–0.75 wt %, an extrudable mixture is formed that can be readily extruded through a 3 mm opening with a temperature rise of no more than a 4° C., and usually less than about 1–2° C.

An anticaking agent can be added, if desired, in an amount sufficient to prevent clumping and caking of the dried extrudates. Generally, anticaking agent is used in an amount within the range of 0.01–1.5 wt % is needed. Silica powder in an amount within the range of 0.5–1.25 wt % is particularly useful.

An amount of solvent is used that is sufficient to form an extrudable mixture of ingredients. Generally, the solvent is used in an amount sufficient to dissolve the polymeric binder and form a lubricious liquid. This lubricious liquid mixture of solvent and dissolved polymer for the active ingredient and any additives used in the formulation. It is believed that the high lubricity of the dissolved polymer acts to reduce the interparticle friction forces and heat that are characteristic of prior extrusion processes. When the solvent is removed, the polymer acts as a structural binder that enhances the structural integrity of the extrudate. Use of a polymer that is soluble in water can help to speed release of the active ingredients following application of the dried particles.

Preferably, the solvent is water, an alcohol-water azeotrope, organic solvents, e.g.: acetonitrile; ethylene dichloride; trichloroethylene; methylene dichloride; benzene; dimethylformamide; tetrahydrofuran; alcohols that are liquid at temperatures within the range of 10°–100° C. such as methanol, isopropanol, and butanol; ketones such as methyl ethyl ketone, toluene, xylene, acetone and methyl isobutyl ketone; dimethylsulfoxide (DMSO); mono- and dialkyl ethers of ethylene glycol and their derivatives sold under the name Cellosolve® by Union Carbide including derivative forms such as Cellosolve® acetate, dimethyl Cellosolve®, butyl Cellosolve®, and diethyl Cellosolve®; anisole; 1,4-dioxane; ethyl acetate; ethylenediamine; mono- and dialkyl ethers of diethylene glycol and their derivatives sold under the name Carbitol® by Union Carbide, and butyl acetate), or a mix of these in an amount of less than 5 wt % based on the total formulation weight. The preferred solvents for use with the preferred polymers, poly(alkylene oxides), are nonaqueous (where the active ingredient is susceptible to hydrolysis) and selected from the group consisting of DMSO, alcohols liquid at 10°–100° C., and alcohol-water azeotropic mixtures.

The solvent for the polymeric binder can be used in an amount within the range of 0.5–4 wt % and more preferably within the range of 1–3 wt %. Some adjustments up or down may be needed to accommodate ambient humidity within the extrusion facility, i.e., high relative humidity may use added water solvent in the lower ranges (e.g., 0.25–2 wt %) while low relative humidity may find it beneficial to use relatively more added water (e.g., 2–5 wt %) to account for evaporation during manufacture. It is desirable, however, to use as little added solvent or water as possible.

Preferably, the polymeric lubricant/binder is dissolved in the solvent at a concentration within the range of 10–20 wt % polymeric solids and sprayed onto the surface of the active ingredient and other granule solids. Spraying enhances distribution of the polymeric lubricant/binder onto the surface of the solids without incurring the energy costs needed to achieve an equivalent distribution with a mixer blade.

In the manufacturing process, an extrudable mixture of active ingredient solids, polymeric lubricant/binder, optional anticaking agent, and a small amount of added solvent is passed through an extrusion die having a suitable diameter, e.g., within the range from about 1–10 mm. The mixture is then extruded into granules.

While the present invention reduces the frictional heat thru the die and extrusion can be performed at any desired temperature, the extrusion process is preferably performed at ambient temperatures (e.g., 15° to 25° C.). Even more preferably, the extrusion is performed in the absence of controlled cooling or heating of the extrusion die and without the introduction of coolant liquid into the formulation. In the present invention, only so much solvent is added as is needed to render the polymeric component lubricious for the extrusion process and effective as a binder in the final granular product.

The extrudate exiting from the extrusion die can be sliced or cut to length before entering a drier to remove excess solvent. Suitable driers include convention ovens, fluidized beds, and the like. Use of a fluidized bed operating at a temperature less than the melting point of the technical grade of active ingredient is particularly preferred. For example, acephate has a melting point within the range of 63°–67° C., so operation of the drier at a temperature of less than 60° C. is preferred when granulating acephate.

Extrudates are often dried to a residual solvent content of less than 1 wt %, preferably to a residual solvent content within the range of 0.01–0.5 wt %, and even more preferably within the range from about 0.01–0.3 wt % based on total weight of the dried extrudate. Usually, no more than about 2–5 minutes is required for adequate drying.

If the extrusion solvent is water and the active ingredient in the granule is sensitive to water or subject to hydrolysis upon storage, it is desirable to dry the extrudate to a residual moisture content of 0.5 wt % or less. It may also be preferable to avoid the use of water altogether and employ a nonaqueous solvent for the polymeric binder to provide adequate lubricity in the extrusion process.

The invention claimed is:

1. An extrudable insecticidally active composition comprising:
    phosphoroamido(di)thioate solids,
    0.2–0.75 total wt % of a poly(alkylene oxide) polymeric lubricant that is normally solid at ambient temperature and dissolved in a solvent, and
    a solvent for said polymeric lubricant in an amount of from 0.5 to less than 5 total wt % but in a quantity sufficient to dissolve said polymeric lubricant and form an extrudable, substantially homogeneous, lubricious mixture of: (i) said phosphoroamido(di)thioate solids, (ii) said polymeric lubricant, and (iii) said solvent.

2. A composition according to claim 1 wherein said composition further comprises 0.01–1.5 total wt % silica powder and 2–4 total wt % water.

3. A composition according to claim 1 wherein said polymeric lubricant comprises poly(ethylene oxide) or poly(butylene oxide).

4. A composition according to claim 1 wherein said solvent is selected from the group consisting of dimethylsulfoxide, alcohols that are liquid at 10°–100° C., and alcohol-water azeotropic mixtures.

5. A composition according to claim 1 wherein the poly(alkylene oxide) has a crystalline melting point within the range from 63° C. to 67° C.

6. A composition according to claim 1 wherein the solvent is present in an amount from 0.5 to 4 total wt %.

7. A composition according to claim 1 wherein said phosphoroamido(di)thioate solids comprise acephate.

8. A composition according to claim 1 wherein said polymeric lubricant comprises poly(ethylene oxide) or poly(butylene oxide).

9. An extrudable insecticidally active composition comprising:
    phosphoroamido(di)thioate solids,
    a poly(alkylene oxide) polymeric lubricant that is soluble in a solvent, normally solid at room temperature, and is present in sufficient quantity to bind together said phosphoroamido(di)thioate solids when said composition is dried to a residual solvent content within the range of 0.01–0.5 total wt %, and
    a solvent for said polymeric lubricant in an amount of from 0.5 to less than 5 total wt % but in a quantity sufficient to dissolve said polymeric lubricant and form an extrudable, luburicious mixture of: (i) said phosphoroamido(di)thioate solids, (ii) said polymeric lubricant, and (iii) said solvent.

10. A composition according to claim 9 wherein said solvent is selected from the group consisting of dimethylsulfoxide, alcohols that are liquid at 10°–100° C., and alcohol-water azeotropic mixtures.

11. A composition according to claim 9 wherein the poly(alkylene oxide) has a crystalline melting point within the range from 63° C. to 67° C.

12. A composition according to claim 9 wherein said composition further comprises 0.01–1.5 total wt % silica powder and 2–4 total wt % water.

13. A composition according to claim 9 wherein the polymeric lubricant is present in an amount within the range from 0.2–0.75 total wt %.

14. A composition according to claim 9 wherein the solvent is present in an amount from 0.5 to 4 total wt %.

15. A composition according to claim 9 wherein said phosphoroamido(di)thioate solids comprise acephate.

16. An insecticidally active solid composition comprising:
    phosphoroamido(di)thioate solids,
    from 0.2 to 3 total wt % of a poly(alkylene oxide) as polymeric lubricant and binder for said composition that is soluble in a solvent and solid at ambient temperatures, and
    a residual amount of a solvent for said polymeric lubricant in an amount of less than 1 total wt %
    wherein,
    said composition has been formed from an extrusion mass by extrusion with a temperature rise of less than 4° C. thru an extrusion die, said extrusion mass comprising:
    (a) said phosphoroamido(di)thioate solids,
    (b) said polymeric lubricant and binder, and
    (c) said solvent for said polymeric lubricant and binder in an amount of less than 5 total wt % but in a quantity sufficient to form a lubricious mixture of: (i) said phosphoroamido(di)thioate solids, (ii) said polymeric lubricant and binder, and (iii) said solvent.

17. A composition according to claim 16 wherein said polymeric lubricant comprises poly(ethylene oxide) or poly(butylene oxide).

18. A composition according to claim 16 wherein said solvent is selected from the group consisting of dimethylsulfoxide, alcohols that are liquid at 10°–100° C., and alcohol-water azeotropic mixtures.

19. A composition according to claim 16 comprising:
    0.1–1 total wt % poly(alkylene oxide),
    0.01–1.5 total wt % silica anticaking agent,
    acephate, and
    less than 1 total wt % solvent for said poly(alkylene oxide).

20. A composition according to claim 16 wherein said phosphoroamido(di)thioate solids comprise acephate.

21. A composition according to claim 16 wherein the poly(alkylene oxide) has a crystalline melting point within the range from 63° C. to 67° C.

22. A composition according to claim 16 wherein the polymeric lubricant is present in an amount within the range from 0.2–0.75 total wt %.

23. A composition according to claim 16 wherein the solvent is present in an amount from 0.001 to 0.5 total wt %.

24. A process for making granules containing insecticidally active solid composition of claim 16, said process comprising the steps of:

extruding homogeneous extrudates from an extrudable lubricated mixture comprising phosphoroamido(di)thioate solids a dissolvable poly(alkylene oxide) lubricant which is present in an amount within the range from 0.2 to 3 total wt %, and a solvent for said dissolvable polymer lubricant in an amount sufficient to dissolve said lubricant and form a lubricious, extrudable mixture, and drying said extrudates to a residual solvent content of less than 1 wt %.

25. An insecticidally active solid composition that has been protected from exposure to heat during manufacture by extrusion at an ambient temperature within the range of 15° to 25° C. with a temperature rise of no more than 4E C when passed through a 3 mm die, said composition comprising:

acephate solids, a poly(alkylene oxide) polymeric lubricant that is soluble in a solvent, solid at ambient temperatures, provides lubricity when dissolved in a solvent, and which acts as a binder for said acephate solids when said solvent is removed, and a residual amount of solvent for said polymeric lubricant in an amount of less than 1 total wt %.

26. An extrudable, insecticidally active composition comprising:

acephate solids, a polymeric lubricant that is soluble in a solvent, normally solid at ambient temperature, provides sufficient lubricity when dissolved in a solvent to allow extrusion of said composition through a 3 mm opening with a temperature rise of no more than 4° C., and which acts as a binder for said acephate solids when said solvent is removed, and a solvent for said polymeric lubricant in an amount of less than 5 total wt % but in a quantity sufficient to dissolve said polymeric lubricant and form a lubricious mixture of: (i) said acephate solids, (ii) said polymeric lubricant, and (iii) said solvent.

* * * * *